United States Patent [19]

Whitman, III

[11] 4,447,709

[45] May 8, 1984

[54] METHOD FOR ELECTRICALLY PERFORATING DIELECTRIC WEBS

[75] Inventor: Hobart A. Whitman, III, Asheville, N.C.

[73] Assignee: Olin Corporation, Pisgah Forest, N.C.

[21] Appl. No.: 106,369

[22] Filed: Dec. 21, 1979

Related U.S. Application Data

[60] Continuation of Ser. No. 745,568, Nov. 29, 1976, abandoned, which is a division of Ser. No. 689,834, May 25, 1976, Pat. No. 4,025,752.

[51] Int. Cl.³ .............................................. H05B 7/18
[52] U.S. Cl. ..................................... 219/384; 318/618
[58] Field of Search ......................... 219/384; 318/618; 83/30, 73, 74; 93/1 G, 58 P; 73/38

[56] References Cited

U.S. PATENT DOCUMENTS

| | | | |
|---|---|---|---|
| 2,372,508 | 3/1945 | Meaker . | |
| 2,528,157 | 10/1950 | Menke | 219/384 |
| 2,528,158 | 10/1950 | Menke | 219/384 |
| 2,678,373 | 5/1954 | Suran | 219/384 |
| 2,955,206 | 10/1960 | Spergel et al. . | |
| 3,045,222 | 7/1962 | Spergel | 318/618 |
| 3,098,143 | 7/1963 | Warmt | 219/384 |
| 3,167,641 | 1/1965 | Parmele et al. . | |
| 3,348,022 | 10/1967 | Schirmer . | |
| 3,364,390 | 1/1968 | Karp et al. | 315/326 |
| 3,371,518 | 3/1968 | Keyes | 73/38 |
| 3,385,951 | 5/1968 | Bancroft et al. | 93/58 P |
| 3,404,687 | 10/1968 | Rickards et al. . | |
| 3,424,895 | 1/1969 | Olson | 219/384 |
| 3,466,925 | 9/1969 | Ziegenhagen et al. | 73/38 |
| 3,502,845 | 3/1970 | Schirmer | 219/384 |
| 3,760,153 | 9/1973 | Davies et al. | 219/384 |
| 3,783,237 | 1/1974 | McArthur | 219/384 |
| 3,862,396 | 1/1975 | Machida et al. . | |
| 4,029,938 | 6/1977 | Martin . | |

OTHER PUBLICATIONS

G. Lago et al., *Control System Theory Feedback Engineering*, 1962, pp. 187–189, 236.

*Primary Examiner*—C. C. Shaw
*Attorney, Agent, or Firm*—Kerkam, Stowell, Kondracki & Clarke

[57] ABSTRACT

A method is provided for controlling the porosity of a web or film issuing from an electric spark perforating apparatus in accordance with an operator-set reference porosity regardless of variations in web speed, inherent web porosity, spark discharge energy and spark repetition frequency by controlling the frequencies of the electrical sparks applied to the web in accordance with the product of two signals, one a difference signal obtained by comparing the porosity of the web leaving the perforator and the reference porosity and the other signal derived from the speed of the web.

3 Claims, 1 Drawing Figure

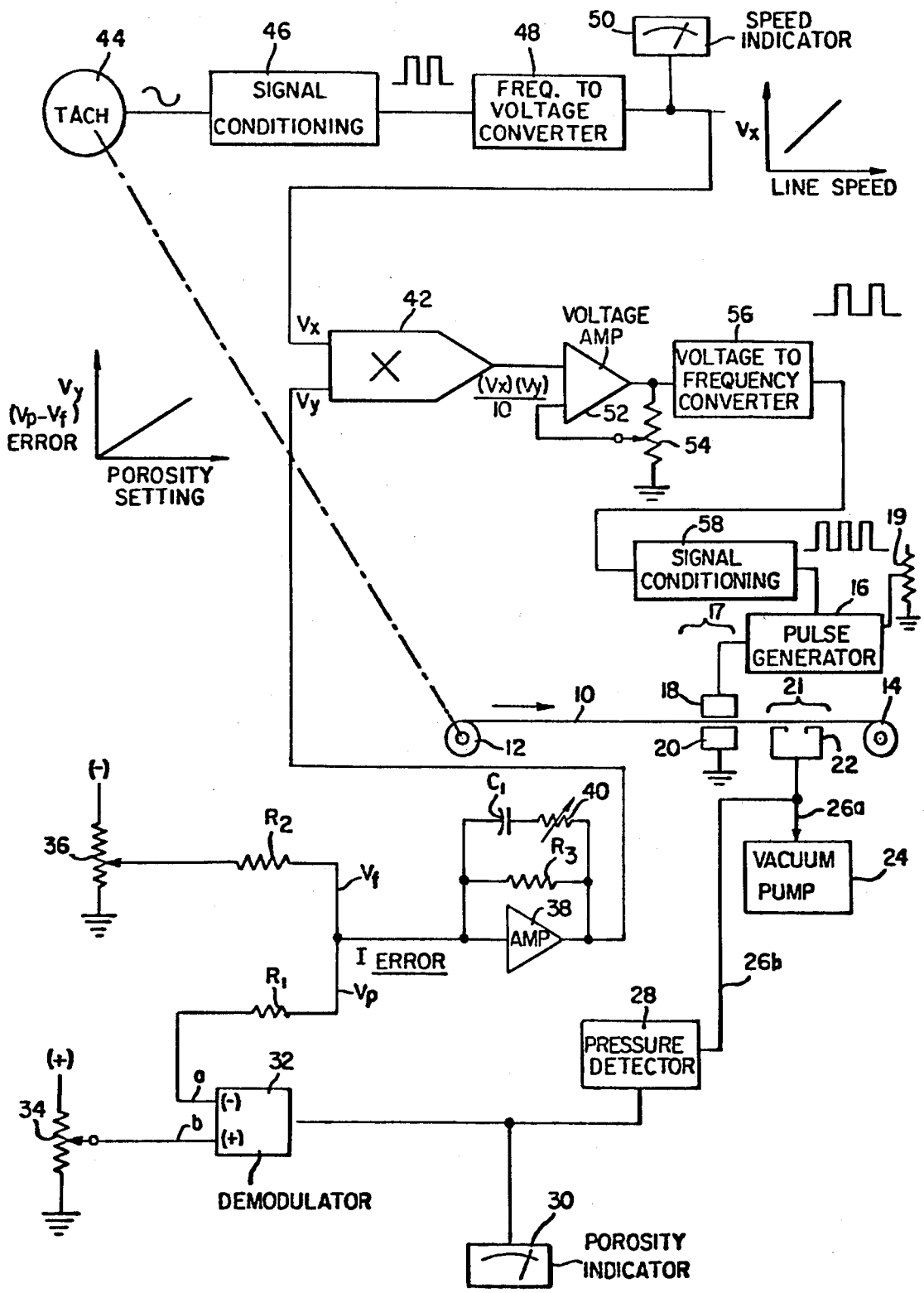

METHOD FOR ELECTRICALLY PERFORATING DIELECTRIC WEBS

CROSS-REFERENCE TO RELATED APPLICATION

This is a continuation of application Ser. No. 745,568, filed Nov. 29, 1976, and now abandoned, which in turn was a division of application Ser. No. 689,834, filed May 25, 1976, now U.S. Pat. No. 4,025,752.

BACKGROUND OF THE INVENTION

1. Field of the Invention

This invention relates generally to a system for controlling the frequency of electrical energization of the electrode or electrodes of apparatus for electrostatically perforating traveling webs of paper, film or a like material to provide a precisely-controlled, uniform porosity of the finished product.

2. Description of the Prior Art

The prior art has disclosed the perforation of a sheet, film or similar article by passing the sheet, typically in web form, between fixed, parallel electrodes having connected thereto a pulse generator for applying periodic pulses to a plate electrode and a ground electrode defining a gap through which the sheet passes, whereby the multiple discharges between the plate electrode and the ground electrode cause perforation of the sheet. The process variables for controlling porosity include: changes in sheet speed, pulsewidth of the energizing pulses, changes in the size of the perforation holes, the degradation of the plate and ground electrodes, change in the position of the aforementioned electrodes and therfore the spark gap established therebetween, drift in spark voltage and current, and changes in the thickness or character of the dielectric materials of the sheet passing through the electrode gap. As will be detailed below, the prior art has essentially ignored many of these parameters, whereby precise control of the sheet's porosity has been difficult, if not impossible.

In U.S. Pat. Nos. 2,528,157 and 2,528,158, there is disclosed apparatus for sensing the porosity of a web or sheet of material moving therepast and for varying the frequency or pulse output of a varactor-type pulse control circuit, whereby the frequency of the discharges between the perforating electrodes between which the sheet is drawn is correspondingly changed. However, such systems ignore the process parameter of varying sheet speed, it being understood that the sheet in the form of a web is drawn from a supply to a take-up roll, past the perforating electrodes.

U.S. Pat. Nos. 2,678,373 and 3,385,951 each disclose apparatus for perforating a moving web of material that is responsive to variations in the sheet speed to vary the rate at which the perforating discharges are generated and applied to the moving web. In U.S. Pat. No. 2,678,373, a tachometer coupled to a roller associated with the moving sheet or web of material provides an output signal indicative of the sheet speed, whereby a relay control system is variably actuated, dependent upon web speed, to selectively couple a predetermined arrangement of capacitive elements to determine the charge repetition rate of the pulse generating circuit. Such a circuit has a disadvantage in that it is not continuously responsive to variations in web speed in that for a discrete range of web speeds, the pulse control circuit is disposed in a single, non-varying configuration to set its pulse or discharge rate for that range. By contrast, U.S. Pat. No. 3,385,951 discloses a perforating apparatus including a tachometer for generating an output signal indicative of web or sheet speed, the tachometer output being applied to a voltage-controlled oscillator, the output of which is of a frequency corresponding to sheet speed. The tachometer output is adjusted by a variable potentiometer, which "provides an adjustment of the slope of the curve of power frequency versus sheet velocity". It is further disclosed that the manual adjustment of this potentiometer will "allow adjustment of the hole size or compensation for changes in web thickness". Such adjustment is carried out manually by the operator, but it is not carried out in an automatic fashion. Thus, unless the operator intervenes to adjust the process by manually varying the potentiometer, no compensation is made for changes in the control parameters such as hole size, spark pulsewidth, deterioration of the electrodes, changes in the position of the electrodes, changes in the power supply and/or changes in the characteristics of the sheet material.

SUMMARY OF THE PRESENT INVENTION

It is therefore an object of the present invention to provide a new and improved system for controlling a system for effecting electrical discharges through a sheet material, compensating for numerous process variables.

It is a further object of the present invention to provide a system for controlling the porosity of a sheet material by controlling electrical discharges therethrough, in accordance with an operator-set reference value of porosity, regardless of variations in web speed, the characteristics of the sheet material, variations is power supply, and sheet speed.

These and other objects of the present invention are met in accordance with teachings of this invention by providing a method for effecting controlled perforations through a sheet or web of material moved therepast by controlling the energization of a pair of electrodes between which the sheet of material is directed in accordance with the product of the measured web speed and of a measurement of the porosity of the web material.

In a preferred embodiment of this invention, measurements of the aforementioned variables are derived and are applied to a multiplication circuit, the output of which is applied to a pulse generator to control the frequency of its output energizing pulses as applied to the pair of electrodes. In an alternative embodiment of this invention, the pulse generator may be varied to control the pulsewidth of the energizing pulses.

In a further aspect of this invention, the measured porosity of the material is compared by summing with a reference signal to derive an error signal, to provide one input to the multiplication circuit. In such a circuit configuration, the error signal is appropriately delayed to take into account the distance between the perforating station at which the pair of electrodes is disposed and the porosity measuring station disposed downstream thereof.

BRIEF DESCRIPTION OF THE DRAWING

The invention will be more particularly described in reference to the accompanying drawing schematically illustrating an embodiment of a control system for controlling the energization of discharges through a sheet material, in accordance with teachings of this invention.

DETAILED DESCRIPTION OF THE PREFERRED EMBODIMENT

With regard to the drawing, there is shown in schematic, block diagram form a system responsive to the velocity of a web or strip 10 of a fibrous or paper material, such as used in the manufacture of cigarettes, as it is drawn from a supply roll 12 to a take-up roll 14, and of a variable indicative of the porosity of the material after it has been perforated at a perforating station 17. As will be explained in detail later, electrical signals indicative of the aforementioned parameters of velocity and porosity are multiplied to obtain a control signal for control of the perforating of the web 10. At the perforating station 17, there is disposed a pair of electrodes 18 and 20, which may illustratively take the form, respectively, of a first set of disks and on endless band ground electrode, as described in the co-pending application entitled, "Apparatus and Method for Electrically Perforating Moving Webs", U.S. Ser. No. 654,201, filed Feb. 2, 1976, in the name of Richard Hugo Martin, now U.S. Pat. No. 4,029,938, and assigned to the assignee of this invention. Illustrative apparatus for transporting the web 10 including the supply and take-up rolls 12 and 14, respectively, also are described in the noted application. In a preferred embodiment of this invention, the first electrode 18 is coupled to a pulse generator 16, responsive to a control signal for controlling the frequency of electrical discharges between the pair of electrodes 18 and 20, whereby the number of holes per linear unit of measurement of the web 10 thus may be controlled. The pulse generator 16 may illustratively take the form of a system of modules including a pulse shaper, a first high voltage pulse and a second, very high voltage pulser, as manufactured by Cober Electronics under their Model No. 2268, and is capable of producing a train of energizing pulses to the first electrode 18 of a voltage that may be varied between 2.5 and 25 KV, and a pulsewidth of 5 to 50 $\mu$sec at a frequency variable from substantially zero to 10 KHz. Illustratively the electrodes 18 and 20 are spaced from each other a distance of approximately 0.020 inch. In a preferred embodiment of this invention, the pulse generator 16 is responsive to the aforementioned control signal to vary the frequency of the energizing electrical signals applied to the first electrode 18, whereby the corresponding frequency of the discharges between the first and second electrodes 18 and 20, and therefore the porosity of the web 10, are determined.

A porosity measuring station 21 is disposed downstream of the perforating station 17, with respect to the movement of the web 10 as indicated by the arrow of the drawing, and includes a chamber 22 in which a vacuum is established by a constant volume vacuum pump 24 as coupled to the chamber 22 by a conduit 26a. It is apparent that as the porosity of the web 10 varies, the degree of vacuum established within the chamber 22 varies and as a result, the pressure as applied via conduits 26a and 26b to a pressure detector 28 varies. The pressure detector 28 is responsive to the variations in pressure to produce an electrical signal to be applied to a demodulator 32, illustratively taking the form of a sine wave carrier demodulator as manufactured by Validyne under their Model No. CD-15. In such an illustrative demodulator 32, there is included a magnetic circuit responsive to the pressure detector output which phase-shifts relative to a high frequency derived from a clock oscillator thereof which in turn is phase-compared with the reference clock signal by mixing to derive a DC output in the range of $\pm$10V DC, as applied to its output terminal "a". As seen in the drawing, the demodulator 32 may be biased variably by a potentiometer 34 so that when the chamber 22 is completely blocked, indicating a zero porosity of the web 10, the output as derived from its terminal "a" is zero.

The output of the demodulator 32 as derived from its terminal "a" is applied to a summing circuit comprised of resistors R1 and R2, whose point of interconnection is applied to the input of an operational amplifier 38. As seen in the drawing, the remote terminal of resistor R2 is connected to the variable contact of a reference potentiometer 36, which is adjusted by the operator to set the desired degree of porosity for the web 10. The summing circuit, comprised of resistors R1 and R2, sums the signal $V_F$ as derived from the reference potentiometer 36, indicative of the desired or reference value of porosity, with the signal $V_P$ indicative of the actual porosity obtained to derive an error signal or current $I_{ERROR}$ to be applied to the operational amplifier 38, illustratively taking the form of an amplifier as manufactured by Analog Devices under their Model No. AD741LH. A relatively high resistance R3 is disposed in parallel between its input and output to ensure a relatively high gain thereof to set the amplitude of the error signal derived from its output, at a relatively high amplitude to be applied to one input of a multiplication circuit 42, as will be set out in detail later. Further, a variable potentiometer 40 and a capacitor C1 disposed in-series with each other, are connected in-parallel between the input and output of the operational amplifier 38 to ensure stability of the measuring circuit by delaying the response of the operational amplifier 38 to the input error signal $I_{ERROR}$, and further to compensate for delay incurred due to the time that it takes for a portion of the web 10 to move from the perforating station 17 to the porosity measuring station 21 so that the output of the operational amplifier as derived, is delayed to take account of this lag in measurement. Typically, the time delay is calculated for the slowest velocity contemplated for the web 10, noting that some variation therein will occur.

The other process variable, the velocity of the web 10, is measured by a tachometer 44 rotatively coupled with the supply roll 12, as indicated by the dashed line in the drawing. As indicated in the drawing, the electrical output signal of the tachometer 44 is in the form of a sinusoidal wave that is applied to a signal conditioning circuit 46 that serves essentially to wave or pulse-shape the sinusoidal wave and illustratively takes the form of a monostable vibrator, the output of which is in the form of a train of pulses, as also indicated in the drawing. The signal conditioned output of the circuit 46 in turn is applied to a frequency-to-voltage converter 48, illustratively taking the form of that circuit as manufactured by the North Hills Corporation under their Model No. FD-10-125, and providing an essentially DC output signal, the amplitude of which is indicative of the frequency of the tachometer output signal. In the illustrative embodiment, the output of the converter 48 varies, typically from zero to 10 V, indicating a web velocity range of zero to 1,000 ft./min. The frequency-to-voltage converter output $V_X$ is applied in turn to a visual speed indicator 50, whereby a visual display thereof is given to the operator, and also to a second input of the multiplying circuit 42, which, in one illustrative embodiment of this invention, may take the form of an IC module, as manufactured by Analog Devices under their Model No. AD532KH.

The output of the multiplier circuit 42 is a product, control signal indicative of the product of the two input signals $V_X$ and $V_Y$, i.e. web velocity and web porosity, and is applied to a voltage amplifier 52, illustratively taking the form of an operational amplifier as manufactured by Analog Devices under their Model No. AD741LH. In turn, the amplifier output is applied to a voltage-to-frequency converter 56, illustratively taking the form of such a circuit module as manufactured by Data Systems under their Model No. VFV-10K, which in turn provides a train of pulses at a frequency proportional to the amplitude of the output signal derived from the voltage amplifier 52. As shown in the drawing, the voltage amplifier output may be adjusted by a variable potentiometer 54, to utilize the entire range of operation of the voltage-to-frequency converter 56. In turn, the voltage-to-frequency converter output is applied to a signal conditioning circuit 58, essentially taking the form of a monostable vibrator, for shaping the pulses into square-waves as shown in the drawing. In turn, the conditioning circuit output is applied to the pulse generator 16. Thus, in one illustrative embodiment, the signal conditioning circuit 58 serves to shape the series of pulses or squarewaves with fine precision so that the pulses illustratively have a pulsewidth of 10 μsec and have a rise time of 200 nanoseconds to a voltage level of 10 V. The pulse generator 16, in response thereto, provides a train of high-voltage pulses to the pair of electrodes 18 and 20 to provide a series of discharges therebetween whereby the web 10 is perforated.

As further shown in the drawing, the pulse generator 16 includes a manually-adjusted variable potentiometer 19, which is set by the operator to choose the pulsewidth of the generator output. Though not shown, a similar control is included to preset the amplitude of the periodic pulses generated by the pulse generator 16. In one illustrative mode of operation, the operator sets the amplitude and the pulsewidth of the train of output pulses from the generator 16, permitting the control system as seen in the drawing to change the frequency of the output to accurately control the porosity for a number of process variables. Illustratively, the operator would set the pulse generator 16 to provide a train of pulses having an amplitude of 5 KV and a pulsewidth of 30 μsec for a web velocity of 1,000 ft./min., such that the output signal would have a value typically varying ±20% about a frequency of 10 KHz, depending upon process variables. Depending upon the particular application, it is noted that the size of the web perforation may be varied by changing the pulsewidth of the energizing signal and this may be accomplished by varying the tap of the petentiometer 19.

In an alternative embodiment of this invention, it is comtemplated that the pulse generator 16 could be adapted to vary the pulsewidth of the energizing output signals, for set, predetermined values of pulse amplitude, and a preset fixed ratio between web speed and pulse frequency, e.g. 50 ft./min. and 1,000 Hz, respectively. It is contemplated that such an embodiment may be preferred, where it is desired to maintain relatively constant the density of the perforations by maintaining the ratio between web speed and the frequency of the pulse generator output substantially constant, e.g. 50 ft./min. and 1,000 Hz, but permitting the size of the perforations to vary. Such an embodiment, it is contemplated, would provide a product with a more even finish or texture.

The significant advantages of using the multiplication circuit 42 to derive the control, product output signal will now be elaborated upon in some detail. First, from an overall philosophy of operation, there is provided a mathematical approach to providing a control signal in view of the units of the system parameters input to the system. In particular, the output of the tachometer 44 is in terms of web velocity in in./sec., while the web porosity is measured in holes/in. When such units are multiplied by the multiplier circuit 42, the control signal units appear as holes/sec., which is precisely the parameter being controlled, i.e. the number of discharges imparted to the web moving thereby in a unit of time.

Further, as will be evident from this discussion, the control system as shown in the drawing, is operative over a wide, continuous range from substantially zero web velocity to the highest web velocity contemplated to achieve a continuous, uniform control of the rate of discharges and thus the porosity of the web 10. Thus, if the apparatus for directing the web 10 is stopped for any of a number of reasons, i.e. apparatus repair or supplying a new roll of the web 10 of material, the control system will continue to function to provide an accurate control of the number of pulses generated between the electrodes 18 and 20. In addition, if the output of the tachometer 44 goes toward zero, a corresponding, substantially zero output is derived from the tachometer 44 which is multiplied with the porosity error signal $V_Y$, to yield a zero output from the multiplier 42, thereby to control the pulse generator 16 to terminate the generation of energizing pulses. In a practical embodiment of this invention, it is noted that as the speed of the web 10 approaches zero, the output of the tachometer 44 may not be precisely accurate, and to this small degree, the output of the pulse generator 16 may differ from a precisely-controlled value. On the other hand, in normal operation, where the measured value of porosity, as derived from the pressure detector 28, is almost that as set upon the reference potentiometer 36, a very small error signal likewise will result and accordingly, the ultimate output resulting from the multiplier 42 and the voltage amplifier 52 will be just sufficient to sustain operation, with the result that little or no correction in the output of the pulse generator 16 will appear.

In another condition of system operation, it is contemplated that the web 10 may break, whereby the measured pressure would indicate an infinite porosity, thereby tending to drive the error signal to a relatively large value. In normal operation, the set or reference point established by the reference potentiometer 36 is slightly greater than the corresponding signal as derived from the demodulator 32. If, however, the output of the demodulator 32 tends to increase to a point greater than the point set by the reference potentiometer 36, a negative $I_{ERROR}$ signal will result, whereby a negative signal is applied to the first input of the multiplier circuit, which in turn will provide a negative signal to the voltage amplifier 52, understanding that a negative signal multiplied by a positive signal will provide a product signal that is negative. In turn, the negative signal as amplified by the voltage amplifier 52, will cause the voltage-to-frequency converter circuit 56 to be driven toward zero, with the result that the pulse generator 16 will terminate the application of its energizing pulses to the electrodes 18 and 20.

Thus, it can be seen that for a wide range of system parameters and conditions, the subject system will operate to provide the desired control of the energizing pulses. In comparison with the prior art, it can be seen that a system incorporating a plurality of capacitors that are selectively connected into the pulse generating circuit at discrete, measured values of web velocity, would provide a discontinuous control of the pulses generated thereby. Further, the system of this invention has significant advantage over that other system described above, utilizing a process of summing a variable indicative of web speed and web porosity, whereby the summed signal is applied to a voltage-controlled oscillator, the output of which determines the frequency of the electrode energizing pulses, in that if the web velocity goes toward zero, there would still be a signal indicative of the set or reference velocity that would tend to drive the associated pulse generator to energize the electrodes, with the result that the web, though stopped, would continue to be subjected to a series of energizing pulses with a significant possibility that the web would be burned.

Thus, there has been shown a new and improved system for achieving control of energization pulses applied between a set of electrodes to perforate a web moved therebetween, in that the precision and uniformity of the output is improved, while still further maintaining the integrity of the control when the material is stopped or when a break in the material occurs. The illustrative embodiment of this invention has been described primarily with regard to the manufacture of cigarette paper, and in this regard, it is noted that the intake of tars and nicotine while smoking is dependent upon the porosity of the cigarette paper. Further, the intake of such tars and nicotine is not a linear function of the porosity, and such intake is increased significantly for a corresponding slight increase in the porosity; therefore, it is a significant advantage to control with great precision the porosity of the cigarette paper whereby the corresponding intake of tars and nicotine may be controlled. Though noting the relative advantages of this system to the manufacture of cigarette paper, it is contemplated that the use of this invention is not so limited and would have like applicability for the perforation of other materials, including cellophane, synthetic polypropylenes and polyethylenes, and other fibrous or paper products such as tea bag paper.

Numerous changes may be made in the above-described apparatus and the different embodiments of the invention may be made without departing from the spirit thereof; therefore, it is intended that all matter contained in the foregoing description and in the accompanying drawings shall be interpreted as illustrative and not in a limiting sense.

What is claimed is:

1. A method of controlling the porosity of a web of sheet material, by controlling a series of periodic electrical pulses applied to a set of electrodes, whereby a corresponding set of electrical discharges is directed through the web, the steps of said method comprising:
   (a) moving the web of sheet material past the set of electrodes;
   (b) measuring the web volocity;
   (c) measuring the porosity of the web;
   (d) deriving a difference signal as a function of the difference between a reference indicative of desired porosity and measured web porosity, the difference signal in normal operation being non-zero and having a magnitude directly related to desired porosity; and
   (e) controllably generating and applying a series of the periodic pulses to the set of electrodes in accordance with the product of the measured web velocity and the difference signal, whereby the porosity of the web is effectively controlled.

2. The method as claimed in claim 1, wherein in step (e), the frequency of the periodic pulses is controlled in accordance with the product of the difference signal and the measured web velocity.

3. The method as claimed in claim 1, wherein in step (e), the pulse width of the periodic pulses is controlled in accordance with the product of the difference signal and the measured web velocity.

* * * * *